United States Patent [19]

Ender

[11] Patent Number: 4,467,793
[45] Date of Patent: Aug. 28, 1984

[54] INSTRUMENTARIUM FOR REDUCING AND FIXING OF PERTROCHANTEROUS AND SUBTROCHANTEROUS FRACTURES AS WELL AS INSERT MEMBER FORMING PART OF THIS INSTRUMENTARIUM

[76] Inventor: Hans G. Ender, Ferstelgasse 6/20, A-1090 Vienna, Austria

[21] Appl. No.: 224,044

[22] PCT Filed: Dec. 12, 1980

[86] PCT No.: PCT/AT80/00035
§ 371 Date: Jan. 12, 1981
§ 102(e) Date: Jan. 12, 1981

[87] PCT Pub. No.: WO81/01647
PCT Pub. Date: Jun. 25, 1981

[30] Foreign Application Priority Data

Dec. 14, 1979 [AT] Austria .................................. 7896/79

[51] Int. Cl.³ .......................... A61F 5/04; A61B 17/18
[52] U.S. Cl. ............................... 128/92 BC; 128/92 B
[58] Field of Search ........... 128/92 BC, 92 B, 92 BA, 128/92 BB, 92 D, 92 R

[56] References Cited

U.S. PATENT DOCUMENTS

| 2,628,614 | 2/1953 | Briggs | 128/92 BA |
| 4,055,172 | 10/1977 | Ender et al. | 128/92 BC |
| 4,169,470 | 10/1979 | Ender et al. | 128/92 BC |

FOREIGN PATENT DOCUMENTS

| 2115289 | 5/1973 | Fed. Rep. of Germany | 128/92 BC |
| 458615 | 8/1968 | Switzerland | 128/92 BB |
| 576249 | 6/1976 | Switzerland | 128/92 BC |

Primary Examiner—Ronald L. Frinks

[57] ABSTRACT

A device for reducing or repositioning and fixing of pertrochanterous and subtrochanterous fractures, comprising at least one bone nail of resilient material, which nail is bent at least at its proximal end portion and which is insertable into the medullary canal of a bone through an impact hole formed in the bone and which is intended to contact, under tension, the apex of the bent portion the wall of the medullary canal, opposing the impact hole. The distal end of the bone nail is provided with a coupling member allowing a positive connection for rotation with an impact tool. An insert member is placed in the impact hole and includes a tubular guide channel through which the bone nails pass and a means to prevent shifting of the insert member in the impact hole.

30 Claims, 8 Drawing Figures

INSTRUMENTARIUM FOR REDUCING AND FIXING OF PERTROCHANTEROUS AND SUBTROCHANTEROUS FRACTURES AS WELL AS INSERT MEMBER FORMING PART OF THIS INSTRUMENTARIUM

CROSS REFERENCE TO RELATED APPLICATION

The invention of this application is disclosed in corresponding International Application No. PCT/AT80/00035 filed Dec. 12, 1980, the benefit of which is being claimed.

BACKGROUND OF THE INVENTION

1. Field of the Invention:

The invention relates to an instrument for reducing or repositioning and fixing of pertrochanterous and subtrochanterous fractures, comprising at least one arcuate bone nail of elastic material, said nail being bent at least at its proximal end portion and being insertable into the medullary canal of the bone via an impact hole arranged in the bone proximally of the knee joint and, in view of its elasticity, contacts under tension with the apex of the bent portion the wall, opposing the impact hole, of the medullary canal and is provided at its distal end with a coupling member allowing on all sides a positive connection for rotation with an impact tool. The invention further relates to an insert member forming part of this instrument.

2. Discussion of the Prior Art

It is already known to reduce or reposition and to fix pertrochanterous and subtrochanterous fractures by opening the bone to form an impact hole and by introducing into this impact hole at least one bone nail, conveniently several bone nails, consisting of elastic material and being bent at least in its proximal area. When introducing such bone nails into the medullary canal, the nails contact, in view of their elasticity, with the apex of the arcuate portion under tension the wall, opposing the impact hole, of the medullary canal. It may be noted that if the proximal point of each nail arrives at the area of the fracture, the nail is passed beyond this fracture and enters the condyle of the bone and is fixed to the fractured area. By rotating the individual nails, the bone portions can be reduced such that they assume the correct relative position at the area of the fracture. For this purpose, the distal end of each nail is provided with a coupling member allowing a wholly non-rotational connection with an impact tool. It is already known to give this coupling member the shape of a small plate-like flattening, but also other embodiments of the coupling member are possible. With the known nails assuming correct position within the medullary canal, the nail ends protrude from the impact hole and the coupling member contacts under tension the outer surface of the bone distally of the impact hole, so that there exists, particularly with older persons having porous bones, the danger that the bone may collapse at the contacting area and additionally the sinews and muscles extending above the impact hole are irritated by the protruding distal nail ends.

As a rule, the impact hole is made such that the bone is first punctured and subsequently the small hole thus formed is widened by means of a three- or four-edged reamer, enlarged by means of a chisel or by means of a drill. In all these cases, parts of the bone can be split off thus enlarging the impact hole in an undesired manner. But also when forcibly driving the nails, a cortical wedge can be split off the proximal cortex by the tangential shearing stress, which results to an undesired enlargement of the impact hole, noting that the edge of the impact hole can also collapse at the forward side. Both cases result in the nails protruding in an uncontrolled manner and, if the fracture extends into the bone, a torsional fracture of the thigh might be produced by the surgeon.

It can also occur that the bone nails are driven too far into the impact hole, so that the coupling member no longer contacts the outer surface of the bone or that the coupling member contacting the outer surface of the bone becomes shifted in direction to the interior of the bone because part of the edge of the hole has been broken away.

If the coupling member enters the interior of the medullary canal and thus disappears within the bone, there results at any rate the drawback that the required tension stress of the nails becomes reduced and that the desired effect is no longer obtained thereby. If the whole nail is located within the medullary canal it might occur that the nail is caught by the spongiosa bubbles present within the medullary canal and is then hindered from sliding in distal direction. If in such a case the bone is loaded such that the bone portions are brought into closer proximity at the area of the fracture it might occur that the nail tip perforates the condyle of the bone and penetrates the socket of the hip joint (acetabulum). If nails having wholly entered the medullary canal are not caught by the spongiosa bubbles, the nails slide in the distal direction and can then be removed only with extreme difficulties. For removing such nails it is at any rate necessary to enlarge the impact hole to such an extent that the distal end located within the medullary canal can be seized.

SUMMARY OF THE INVENTION

It is an object of the invention to avoid these drawbacks. The invention is based on an instrument of the type initially described and essentially consists in that an insert member is provided and adapted for being inserted into the impact hole, said insert member having a guiding channel for the bone nail or bone nails, respectively, and accommodating at least partially the coupling member of the bone nail or nails and being provided with a fixing means preventing the insert member from becoming shifted within the impact hole. This insert member, which is inserted into the impact hole and is fixed therein by the fixing means, prevents the impact hole from becoming spalled when driving in the nails and thus from becoming enlarged in a disadvantageous manner and the size of the openings through which the bone nails are driven into the medullary canal is rather defined by the cross section of the guiding channel. Furthermore, by using such an insert member, the nails can be driven into the bone to such a depth that their distal end is accommodated by the insert member and thus, does not protrude, so that any irritation of the muscles and sinews is prevented and additionally, entering of the nail ends, provided with the coupling member, into the medullary canal is avoided. The forces exerted by the coupling members of the nails subjected to tension stress are rather supported by the insert member and transmitted by this insert member on the bone in an equal manner over the whole circumference of the impact hole so that even with older humans having porous bones any danger of a break down of the bone at the area of the impact hole is avoided. Finally, the nails are, on forcibly driving the nails, guided at the driving-in position by the guiding channel of the insert member, so that also when driving-in the nails there exists no danger of injuring the bone by subjecting the proximal cortex to tangential shearing stress. In view of the distal ends, provided with the coupling members and the nails being arranged within the insert member and thus being easily accessible, the nails can easily be removed from the medullary canal when using an instrument according to the invention.

As already mentioned, the insert member must be provided with a fixing means for preventing any shifting movement of the insert member, i.e. for preventing the insert member from falling out of the impact hole or from excessive penetration into the medullary canal. Therefore, and according to a preferred embodiment of the invention, the insert member consists of a tubular or channel-shaped section comprising an outwardly protruding flange contacting the outer surface of the bone. This flange acts as an abutment and prevents, when contacting the outer surface of the bone, the insert member from becoming shifted in direction to the medullary canal. The tubular section wholly encloses the distal ends of the bone nails. In view of the ends of the bone nails only contacting the distal area of the section, since the bone nails are tensioned, it is even sufficient to give this section the shape of a channel being open in proximal direction without substantially detracting from the desired effect.

The axis of the tubular or channel-shaped section preferably forms an acute angle with the plane of the flange, so that by correspondingly arranging the insert member within the impact hole, the guiding channel defined by the tubular or channel-shaped section assumes such a position that the nails introduced assume their correct position within the medullary canal. For ensuring a correct position of the insert member it is equally required to prevent the insert member from any rotational movement and from sliding out of the impact hole, above all, when forcibly introducing the nails. Therefore, the insert member conveniently has a projection contacting the wall of the medullary canal and preventing the insert member from both an unintended dropping out of the insert member from the impact hole and, by frictional connection, an unintended rotation of the insert member. These projections can, for example, be formed of resilient tongues which yield when inserting the insert member into the impact hole but which, with the insert member assuming its correct position, resiliently return and grip behind the edge of the impact hole. Conveniently, these tongues are formed of portions bent out of the tubular or channel-shaped section. In this case, the tongues can be distributed over the whole circumference and can easily be manufactured, for which purpose, for example, only punching operations need be effected on the tubular or channel-shaped section. However, the part of the insert member forming the guiding channel can also be designed in the manner of a known straddling dowel, so that this part can on corresponding operation be straddled within the impact hole and thus the insert member can neither be rotated nor be removed. Finally, it is in the most simple case also possible to provide on the flange at least one opening for inserting therethrough a screw or the like adapted for being anchored within the bone and providing a safety means against unintended rotation and unintended removal of the insert member.

For reliably preventing unintended outward movement of the distal nail ends from the insert member, the guide channel of the insert member can, according to a further feature of the invention, be closable by a closure means. This closure means can, for example, consist of a lid preferably provided with a collar extending into the guiding channel. For reliably connecting this lid with the insert member, the lid can be adapted to be connected with the insert member by means of a bayonet lock or the lid can be provided with a thread cooperating with a corresponding thread arranged within the insert member. It is also possible to give the collar a conical shape and to fix it within the guiding channel by force fitting.

It is further possible to close the guiding channel of the insert member by casting into this guiding channel and thereby at least partially filling this guiding channel with a settable material, preferably a settable synthetic plastics material, after having inserted the nails. The distal nail ends are thus fixed in their position such that they are not allowed any shifting movement whatsoever. For reliably anchoring this material within the guiding channel after having set, the guiding channel is, according to the invention, provided with elevations such as grooves or the like within the portion which is to receive the setting material by casting.

BRIEF DESCRIPTION OF THE DRAWINGS

In the drawings, the embodiments of the invention are schematically illustrated.

DESCRIPTION OF THE PREFERRED EMBODIMENTS

Figure 1:
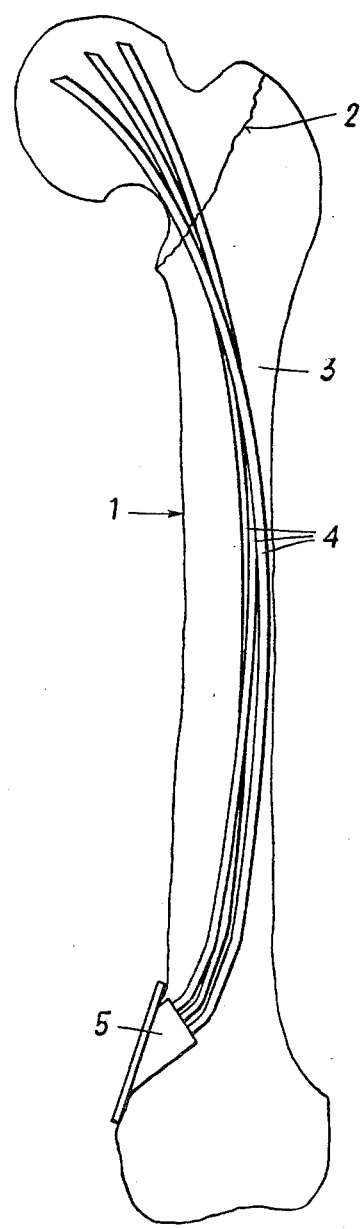
FIG. 1 is a schematic view showing an insert and bone nails according to the invention as arranged within a bone having a fracture.

In FIG. 1 a bone 1 is shown comprising a fracture 2. For reducing or repositioning and fixing the fracture 2, three bone nails 4 consisting of elastic material and being bent in their proximal end portion are inserted into the medullary canal 3 of the bone 1. For this purpose, the medullary canal is punctually punctured at the area of the joint portion of the bone and subsequently an impact hole is milled or bored by means of a milling cutter or a drill, thereby selecting the axis of the hole such that the nails 4 can be forcibly driven in the required direction. Subsequently, an insert member 5 is inserted into the impact hole whereupon the bone nails 4 are forcibly introduced and rotated for reducing or repositioning the fractured area. For this purpose, the bone nails are provided at their respective distal end with a coupling member not shown allowing a wholly non-rotatable connection with an impact tool. Conveniently, this coupling member is formed of a small plate-like flattening of the distal nail end and provided with a slot which enables removal of inserted nails. The insert member 5 has a guide channel 6 (see FIGS. 2 to 7) which is arranged such that the nails, when forcibly introduced, run into the medullary canal 3 in the desired manner. Furthermore, the insert member 5 is provided with a flange 7 contacting the outer surface of the bone and preventing the insert member 5 from entering the medullary canal for too great a distance. The nails 4 are introduced to such a depth that their distal end, provided with the coupling member, is accommodated within the guiding channel, i.e. is not outwardly protruding and irritating overlying sinews and muscles, but it also does not slide into the medullary canal.

Figures 5, 8:
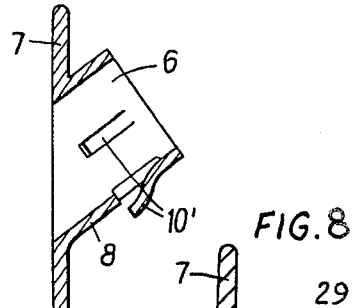
Figure 6:
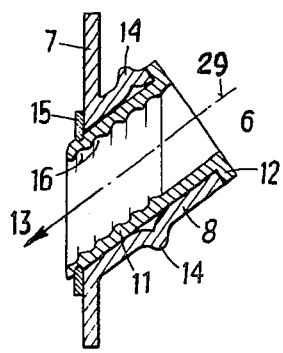
Figure 7:
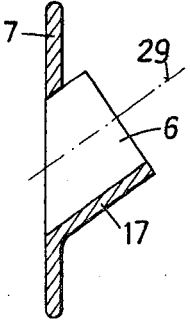

With the embodiments according to FIGS. 3 to 6, the guiding channel 6 is formed of a tubular piece 8 connected with the flange 7, and with the embodiment according to FIG. 7, the guiding channel is formed of a channel-shaped section 17 which is open in proximal direction. The axis 29 of this tubular piece 8 and of the channel-shaped section 17, respectively, includes an acute angle α with the plane of the flange 7, so that the guiding channel 6 assumes, with the insert member 5 being correctly positioned within the impact hole, the correct position for introducing the bone nails 4. For maintaining this position, it is convenient to fix the insert member 5 to prevent both rotation as well as unintended sliding out of the impact hole. In the embodiment of the insert member according to the FIGS. 2 and 3, an opening 9 is, for the mentioned purpose, provided within the flange 7 for passing therethrough a screw which can be screwed into the bone. A plurality of openings can be provided in combination with a plurality of screws. In the embodiment according to FIG. 4, the insert member has a projection formed of a resilient tongue 10 which contacts the inner wall of the medullary canal as soon as the insert member has been positioned. This resilient tongue 10 is with one end fixed on the outer side of the tubular piece 8 and designed at its other end such that it contacts the outer surface of the tubular section 8 when the insert member is introduced into the impact hole but resiliently springs back and then approximately assumes the position shown in FIG. 4 in which position the tongue grips behind the edge of the impact hole and thus fixes the insert member 5.

In the embodiment shown in FIG. 5, a plurality of resilient tongues 10' are provided which are formed of outwardly bent punched portions of the tubular piece 8. Such resilient tongues 10' can be manufactured in a very economical manner.

In the embodiment according to FIG. 6, a bushing 11 is arranged within the tubular section 8 and provided with a projection 12. With this embodiment, the tubular section 8, and conveniently also the flange 7, are produced of yielding material, for example of synthetic plastic material. After having introduced the insert member 5 into the impact hole, the bushing 11 is pulled in direction of the arrow 13, whereby the tubular section 8 becomes widened at 14 and grips behind the impact hole and its inner side, thus fixing the insert member in position. The position of the bushing 11 can, for example, be fixed by a circlip 15 or the like.

For reliably preventing the distal ends of the nails from subsequently projecting outwardly from the insert member 5, it is convenient to close this insert member. This can, for example, be effected by pouring a hardening material, for example, a setting synthetic plastic material into the insert member. This material, after having become hardened, fixes the distal nail ends in a non-displaceable manner. For reliably securing this material, after having become hardened, within the guiding channel 6, this guiding channel is at least partially provided with elevations, preferably grooves 16, as is shown in FIG. 6 for the bushing.

Figure 3:
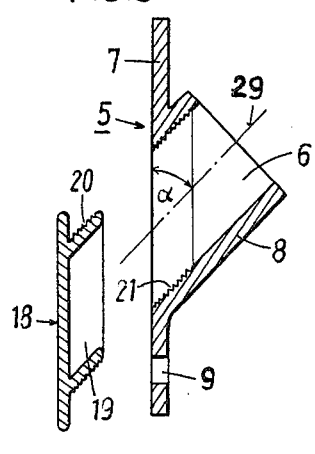
FIG. 3 is a cross-sectional view taken along line III—III of FIG. 2.
Figure 2:
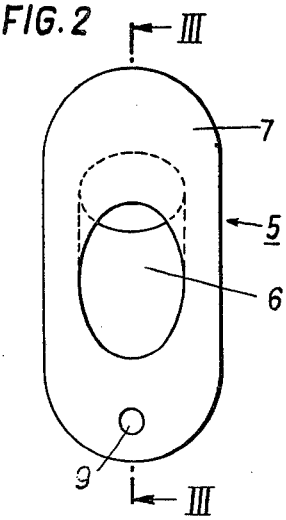
FIG. 2 shows the insert member according to the invention as shown in FIG. 1 in a front elevation.
Figure 4:
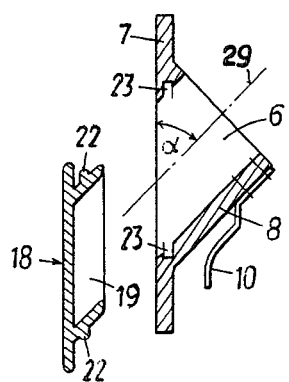
FIGS. 4 to 8 are cross-sectional views showing modified embodiments of the insert member corresponding to the section shown in FIG. 3.

The guiding channel 6 can, however, also simply be closed by a lid 18 as is indicated in FIGS. 3 and 4. In the embodiment according to FIG. 3, the lid 18 is provided with a collar 19 having an outer thread 20 cooperating with an internal thread 21 within the guide channel. In the embodiment according to FIG. 4, the collar 19 has protruding pins 22 which are insertable into recesses 23 within the flange 7 which recesses are arranged within the flange 7 as for a bayonet lock. The collar 19 can, however, simply be conical in shape and press-fitted within the guide channel 6. In all cases, the lid 18 is reliably anchored within the insert member 5.

With all embodiments, the insert member can consist of stainless steel or of synthetic plastic material or of a combination of these materials.

What is claimed is:

1. A device for reducing and fixing pertrochanterous and subtrochanterous fractures, comprising:
    at least one resilient bone nail, said at least one bone nail being arcuate at least at its proximal end portion and including a coupling member at its distal end adapted to be rotated by a tool, said at least one bone nail being adapted for insertion into the medullary canal of a bone through an impact hole therein; and
    an insert member adapted to be inserted in the impact hole, said insert member having a guiding channel therein adapted to permit passage therethrough of said at least one resilient bone nail and to at least partially accomodate the coupling member, said insert member also integrally including a means adapted to fix said insert member in the impact hole and to prevent it from shifting therein.

2. A device as claimed in claim 1, whereinthe insert member comprises a tubular section having an outwardly radiating flange adapted to contact the outside of the bone.

3. A device as claimed in claim 2, wherein the axis of the tubular section forms an acute angle with the plane of the flange.

4. A device as claimed in claim 1, wherein the insert member has at least one projection adapted to contact the wall of the medullary canal.

5. A device as claimed in claim 4, wherein the projection is formed of at least one resilient tongue.

6. A device as claimed in claim 5, wherein the said at least one tongue is formed of parts bent out of the tubular section.

7. A device as claimed in claim 1, wherein the part of the insert member which forms the guiding channel is designed in the manner of a straddling dowel.

8. A device as claimed in claim 2, wherein at least one opening is provided within the flange for passing therethrough a screw adapted to be anchored within the bone.

9. A device as claimed in claim 1, wherein the guiding channel of the insert member is closed by a closure means.

10. A device as claimed in claim 9, wherein the closure means is formed of a lid.

11. A device as claimed in claim 10, wherein the lid engages the insert member by means of a bayonet lock.

12. A device as claimed in claim 10, wherein the lid is provided with a threaded portion cooperating with a theaded portion provided in the insert member.

13. A device as claimed in claim 10, wherein said lid is provided with a collar which projects into the guiding channel.

14. A device as claimed in claim 13, wherein the collar of the lid is conically shaped and fixed within the guiding channel by force-fitting.

15. A device as claimed in claim 9, wherein the guiding channel at least partially includes a hardening material, which hardening material is placed therein after insertion of said at least one nail.

16. A device as claimed in claim 15, wherein the guiding channel is provided with elevations within the portion which receives the hardening material.

17. A device as claimed in claim 15, wherein said hardening material is a synthetic plastic.

18. A device as claimed in claim 16, wherein the elevations take the form of grooves.

19. An insert member adapted to be inserted in an impact hole formed in the medullary canal of a bone and further adapted to be used in conjunction with at least one bone nail having a coupling member at its distal end in reducing and fixing pertrochanterous and subtrochanterous fractures, said insert member having a guiding channel adapted for passage of bone nails therethrough and for accommodating coupling members therein, means adapted to fix said insert member in the impact hole and to prevent it from shifting therein, and a closure means for closing said guide channel.

20. Insert member as claimed in claim 19, wherein said closure means is formed of a lid.

21. Insert member as claimed in claim 20, wherein said lid engages the insert member by means of a bayonet lock.

22. Insert member as claimed in claim 20, wherein said lid is provided with a threaded portion cooperating with a threaded portion provided in the insert member for retaining said lid on said insert.

23. Insert member as claimed in claim 20, wherein said lid is provided with a collar which projects into the guiding channel.

24. Insert member as claimed in claim 23, wherein the collar of the lid is conically shaped and is fixed within the guiding channel by force-fitting.

25. Insert member as claimed in claim 19 and further comprising a casting of a hardening material, at least partially filling said guiding channel to retain the ends of the bone nails therein.

26. Insert member as claimed in claim 25, wherein said guiding channel is provided with elevations within the portion which receives the hardening material.

27. Insert member as claimed in claim 25, wherein said hardening material is a synthetic plastic.

28. Insert member as claimed in claim 26, wherein said elevations are in the form of grooves.

29. An insert member adapted to be inserted in an impact hole formed in the medullary canal of a bone and further adapted to be used in conjunction with at least one bone nail having a coupling member at its distal end in reducing and fixing pertrochanterous and subtrochanterous fractures, said insert member comprising a tubular section adapted to be inserted into said impact hole, a guiding channel through said tubular section adapted for passage of bone nails therethrough and for accommodating coupling members therein, and at least one resilient tongue formed of a part bent out of said tubular section and projecting therefrom adapted to contact the wall of the medullary canal to fix said insert member in the impact hole and to prevent it from shifting therein.

30. An insert member adapted to be inserted in an impact hole formed in the medullary canal of a bone and further adapted to be used in conjunction with at least one bone nail having a coupling member at its distal end in reducing and fixing pertrochanterous and subtrochanterous fractures, said insert member having a guiding channel designed in the manner of a straddling dowel adapted for passage of bone nails therethrough and for accommodating coupling members therein, and means adapted to fix said insert member in the impact hole and to prevent it from shifting therein.

* * * * *